(12) United States Patent
Balda et al.

(10) Patent No.: US 12,150,767 B2
(45) Date of Patent: Nov. 26, 2024

(54) PATCH STACK-UP

(71) Applicant: Medicomp, Inc., Melbourne, FL (US)

(72) Inventors: Anthony Balda, Melbourne, FL (US); Sean Marcus, Rockledge, FL (US); George Koos, Melbourne Beach, FL (US); Sara Fabiola England Lopera, Melbourne, FL (US); Monte Marek, Palm Bay, FL (US)

(73) Assignee: Medicomp, Inc., Melbourne, FL (US)

( * ) Notice: Subject to any disclaimer, the term of this patent is extended or adjusted under 35 U.S.C. 154(b) by 1323 days.

(21) Appl. No.: 16/339,452

(22) PCT Filed: Nov. 1, 2016

(86) PCT No.: PCT/US2016/059921
§ 371 (c)(1),
(2) Date: Apr. 4, 2019

(87) PCT Pub. No.: WO2018/084832
PCT Pub. Date: May 11, 2018

(65) Prior Publication Data
US 2019/0290160 A1 Sep. 26, 2019

(51) Int. Cl.
*A61B 5/05* (2021.01)
*A61B 5/00* (2006.01)
(Continued)

(52) U.S. Cl.
CPC .............. *A61B 5/259* (2021.01); *A61B 5/282* (2021.01); *A61B 5/30* (2021.01); *A61B 5/6833* (2013.01);
(Continued)

(58) Field of Classification Search
CPC ....... A61B 5/282; A61B 5/0006; A61B 5/259; A61B 2560/0412; A61B 2562/0215; A61B 5/6833; A61B 5/291; A61B 5/6831
(Continued)

(56) References Cited

U.S. PATENT DOCUMENTS 7,206,630 B1 * 4/2007 Tarler ..................... A61B 5/398
600/509
8,315,687 B2 11/2012 Cross et al.
(Continued)

OTHER PUBLICATIONS

International Search Report and Written Opinion for related application PCT/US2016/59921 dated Jan. 24, 2017; 16 pages.
(Continued)

*Primary Examiner* — Joseph A Stoklosa
*Assistant Examiner* — Brian M Antiskay
(74) *Attorney, Agent, or Firm* — Carlson, Gaskey & Olds, P.C.

(57) ABSTRACT

A system for biometric monitoring may include a patch, a plurality of electrodes, a flexible printed circuit, and a cradle. The patch may be adapted to adhere to a patient's skin. The plurality of electrodes may be carried by the patch. The flexible printed circuit may be carried by the patch and include an electrical pad and a trace adapted to provide electrical communication between the plurality of electrodes and the electrical pads. The cradle may be affixed to the patch. A back side of the flexible printed circuit directly opposing the electrical pad may be affixed to the front surface of the cradle. The electrical pad may be adapted to electrically engage an electrical contact located on a biometric monitoring device carried by the cradle.

17 Claims, 6 Drawing Sheets

(51) Int. Cl.
*A61B 5/259* (2021.01)
*A61B 5/282* (2021.01)
*A61B 5/30* (2021.01)

(52) U.S. Cl.
CPC ..... *A61B 5/7225* (2013.01); *A61B 2560/0443* (2013.01); *A61B 2562/0217* (2017.08); *A61B 2562/164* (2013.01); *A61B 2562/166* (2013.01)

(58) Field of Classification Search
USPC .................. 600/372, 382–393, 508–509
See application file for complete search history.

(56) References Cited

U.S. PATENT DOCUMENTS

| | | | |
|---|---|---|---|
| 8,560,040 B2 | 10/2013 | Gehman et al. | |
| 9,364,150 B2 | 6/2016 | Sebelius et al. | |
| 9,585,584 B2 | 3/2017 | Marek et al. | |
| 2007/0270678 A1* | 11/2007 | Fadem | A61B 5/282 600/372 |
| 2014/0275932 A1* | 9/2014 | Zadig | A61B 5/02438 600/386 |
| 2015/0073231 A1 | 3/2015 | Beck et al. | |
| 2015/0073251 A1* | 3/2015 | Mazar | A61B 5/318 600/391 |
| 2015/0250422 A1* | 9/2015 | Bay | A61B 5/24 600/391 |

OTHER PUBLICATIONS

Extended European Search Report and Written Opinion for related European application 16920518.4 dated Apr. 3, 2020; 7 pages.
Office action in related Canadian patent application dated Jan. 5, 2024; 4 pages.

* cited by examiner

PATCH STACK-UP

RELATED APPLICATIONS

This application is a national phase application of and claims priority under 35 U.S.C. § 371 of PCT U.S. Patent Application Serial No. PCT/US16/59921 filed on Nov. 1, 2016 and titled PATCH STACK-UP. The content of this application is incorporated herein by reference.

FIELD OF THE INVENTION

The present invention relates generally to systems and methods for medical monitoring of physiological signals and parameters and, more particularly, to wearable devices with integrated ECG sensors for ambulatory ECG monitoring, and related systems and methods.

BACKGROUND

Heart disease is a leading cause of death in the United States. Some patients may benefit from long-term ECG monitoring outside of a clinical setting. For example, atrial fibrillation and myocardial ischemia may occur episodically. Some episodes may occur without patient symptoms. Myocardial ischemia, if persistent and serious, can lead to myocardial infarction (heart attack). During a myocardial infarction, electrophysiological changes may be detected by an ECG monitoring device. For accurate diagnosis and effective treatment of many episodic heart conditions, medical professionals need to receive accurate and timely information regarding the frequency and duration of such episodes.

In conventional long-term ECG monitoring, such as with continuous Holter monitors or event monitors, mounting of the monitor typically involves preparation of the patient's skin to receive the monitoring device. Chest hair may be shaved or dipped from men. The skin is abraded to remove dead skin cells, and cleaned. A technician trained in electrode placement applies the electrodes to the skin with an adhesive. Each electrode of such conventional monitors is attached to an insulated wire that is routed some distance across the patient's body to an amplifier designed to amplify the ECG signal in preparation for further processing, Such monitoring systems are often worn by a patient for up to a month.

Traditional long-term monitoring systems like those described above present a number of problems. For example, abrading in preparation for electrode mounting often leaves the patient's skin irritated, During use, the patient must be careful not to pull on the wires connected to the electrodes, lest the electrodes be pulled off the skin. Removing an electrode with its strong adhesive may be painful to the patient. Furthermore, certain types of electrodes require use of a gel next to the skin to improve conductivity at the point of connection of the metal electrode to the skin. Prolonged exposure to the gel can irritate the skin. These and other discomfort factors associated with traditional long-term monitoring solutions may discourage a patient from using the ECG monitor as directed by medical personnel.

Alternative health monitoring system designs exist that attempt to address the many shortcomings of traditional ECG monitors. For example, some monitor implementations known in the art are based on an article of apparel designed to be conveniently and comfortably worn by the patient, such as a wrist band or finger ring. Also for example, some monitors are implemented as earphones equipped with sensors and data communications means. However, the still-prominent profile of such monitors still may make wear of the devices uncomfortable and use of such devices error-prone. Furthermore, currently available types of medical/health monitoring solutions typically require separate devices for monitoring different physiological parameters. At best, some existing devices are capable of limited simultaneous monitoring or interchangeability.

U.S. Patent Application Publication No. 201410243612 by Li et al. discloses a portable handheld device for simultaneously monitoring pulse waveforms indicative of blood pressure, blood oxygen levels, and electrocardiogram (ECG) signals. Data from the device may be analyzed onboard, with local computerized devices, and with remote server based systems. However, this multifunctioning handheld device requires the user to hold it in place and is not suited to long-term wear.

No device currently exists that supports seamless interchangeability between multiple monitoring types and can be worn for extended periods. Consequently, a need exists for increasingly comfortable and convenient monitoring devices for both personal and medical use, and that overcome the shortcomings of common implementations in the field.

This background information is provided to reveal information believed by the applicant to be of possible relevance to the present invention. No admission is necessarily intended, nor should be construed, that any of the preceding information constitutes prior art against the present invention.

SUMMARY OF THE INVENTION

With the above in mind, embodiments of the present invention are related to a system for biometric monitoring including a patch, a plurality of electrodes, a flexible printed circuit, and a cradle. The patch may have a first side adapted to adhere to a patient's skin and an opposing second side. The plurality of electrodes may be carried by the patch and adapted to be in electrical communication with the patient's skin. The flexible printed circuit may be carried by the patch and may include an electrical pad and a trace. The electrical pad may be located on a front side of the flexible printed circuit. The trace may be located on the front side and adapted to provide electrical communication between one of the plurality of electrodes and the electrical pad. The cradle may have a back surface affixed to the patch and an opposing front surface, A back side of the flexible printed circuit directly opposing the electrical pad may be affixed to the front surface of the cradle. The electrical pad may be adapted to electrically engage an electrical contact located on a biometric monitoring device carried by the cradle.

The plurality of electrodes may include a first electrode and a second electrode with a center positioned at least 8 centimeters away from a center of the first electrode. The patch may include one or more of a plurality of arcuate edge portions. A first arcuate edge portion may extend around the first electrode. A second arcuate edge portion may extend around the second electrode. A third arcuate edge portion may extend between a first side of the first electrode and a first side of the second electrode, A fourth arcuate edge portion may extend between a second side of the first electrode and a second side of the second electrode. A fifth arcuate edge portion may extend between the fourth arcuate edge portion and the second arcuate edge portion.

The patch may include a linear top edge extending parallel to a line segment extending between the first arcuate edge portion and the fourth arcuate edge portion. The patch may include one or more of a plurality of notches. A first notch may be located in the patch perimeter adjacent the first arcuate edge portion and the third arcuate edge portion. A second notch may be located in the patch perimeter adjacent the second arcuate edge portion and the third arcuate edge portion. A third notch may be located in the patch perimeter adjacent the first arcuate edge portion and the fourth arcuate edge portion. In one embodiment, a third notch may be located in the patch perimeter adjacent the first arcuate edge portion and the linear top edge. A fourth notch in the patch perimeter may be located adjacent the second arcuate edge portion and the fourth arcuate edge portion. In one embodiment, a fourth notch may be located in the patch perimeter adjacent the second arcuate edge portion and the fifth arcuate edge portion. A fifth notch in the patch perimeter may be located adjacent the linear top edge and the fourth arcuate edge portion. A sixth notch in the patch perimeter may be located adjacent the fourth arcuate edge portion and the fifth arcuate edge portion.

The plurality of electrodes may include a third electrode located in a linear configuration between the first electrode and the second electrode. The plurality of electrodes may also include a fourth electrode positioned substantially normal to the third electrode and the line segment joining the first electrode and the second electrode.

The patch may include a first layer and a second layer. The first layer may have a first perimeter and be adapted to be located adjacent the patient's skin. The second layer may be adhered to the first layer and contained entirely within an area defined by the first perimeter.

The cradle may be adhered to the second layer and contained entirely within an area defined by a perimeter of the second layer. The first layer may include a non-woven material. The second layer may have a second perimeter between 5.4 millimeters and 6.6 millimeters from the first perimeter along the entirety of the second perimeter.

A portion of the flexible printed circuit may be carried between the first layer and the second layer. The second layer may have an aperture adapted to receive a portion of the flexible printed circuit. The second layer may include a foam material. Each point of a perimeter of each of the plurality of electrodes may be at least 1 centimeter away from a perimeter of the second layer.

DETAILED DESCRIPTION OF THE INVENTION

Figure 1:
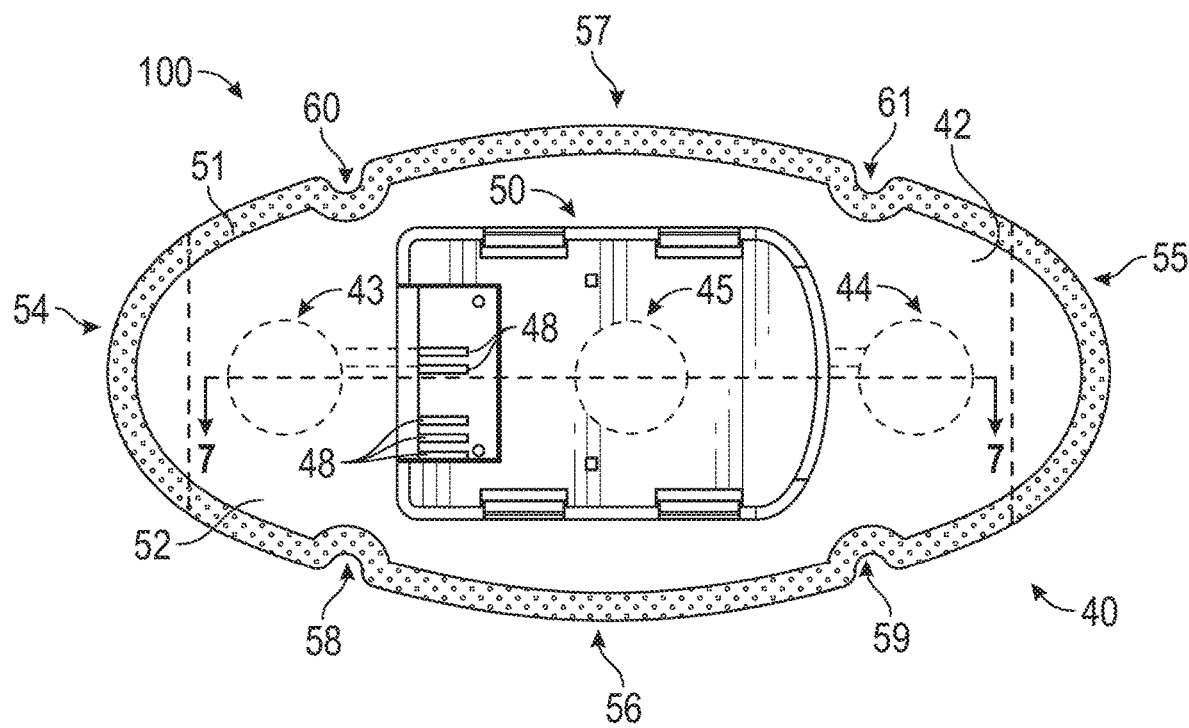
FIG. 1 is a top plan view of a system for biometric r onitoring according to an embodiment of the present invention.
Figure 2:
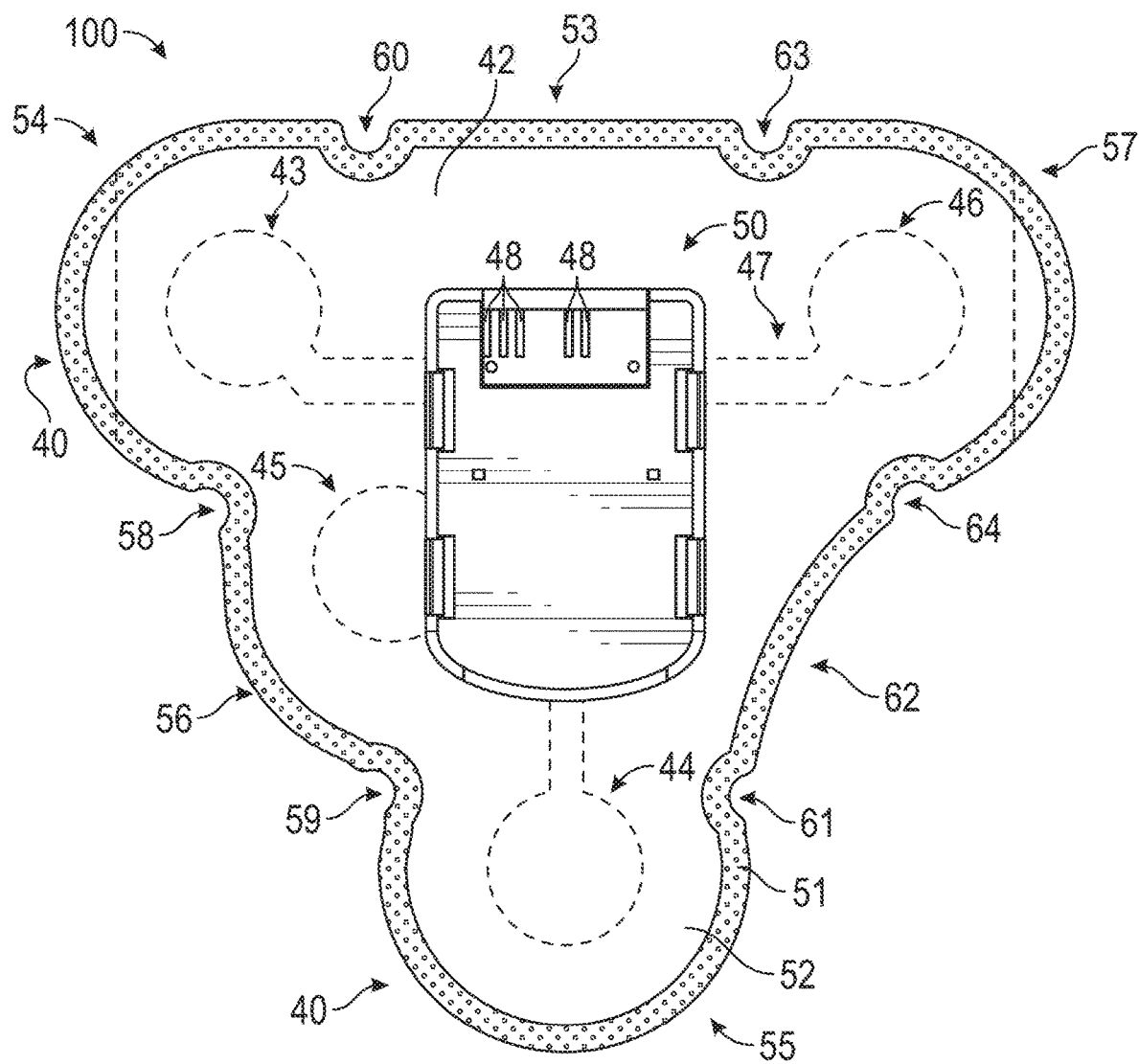
FIG. 2 is a top plan view of a system for biometric monitoring according to another embodiment of the present invention.
Figure 3:
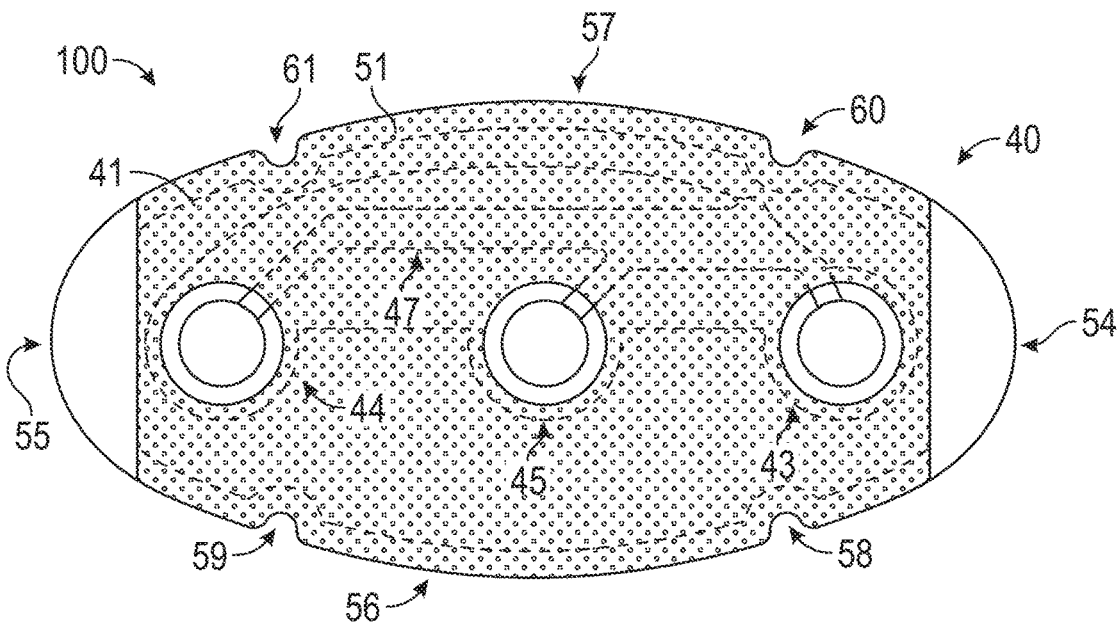
FIG. 3 is a bottom plan view of the system for biometric monitoring as depicted in FIG. 1.
Figure 4:
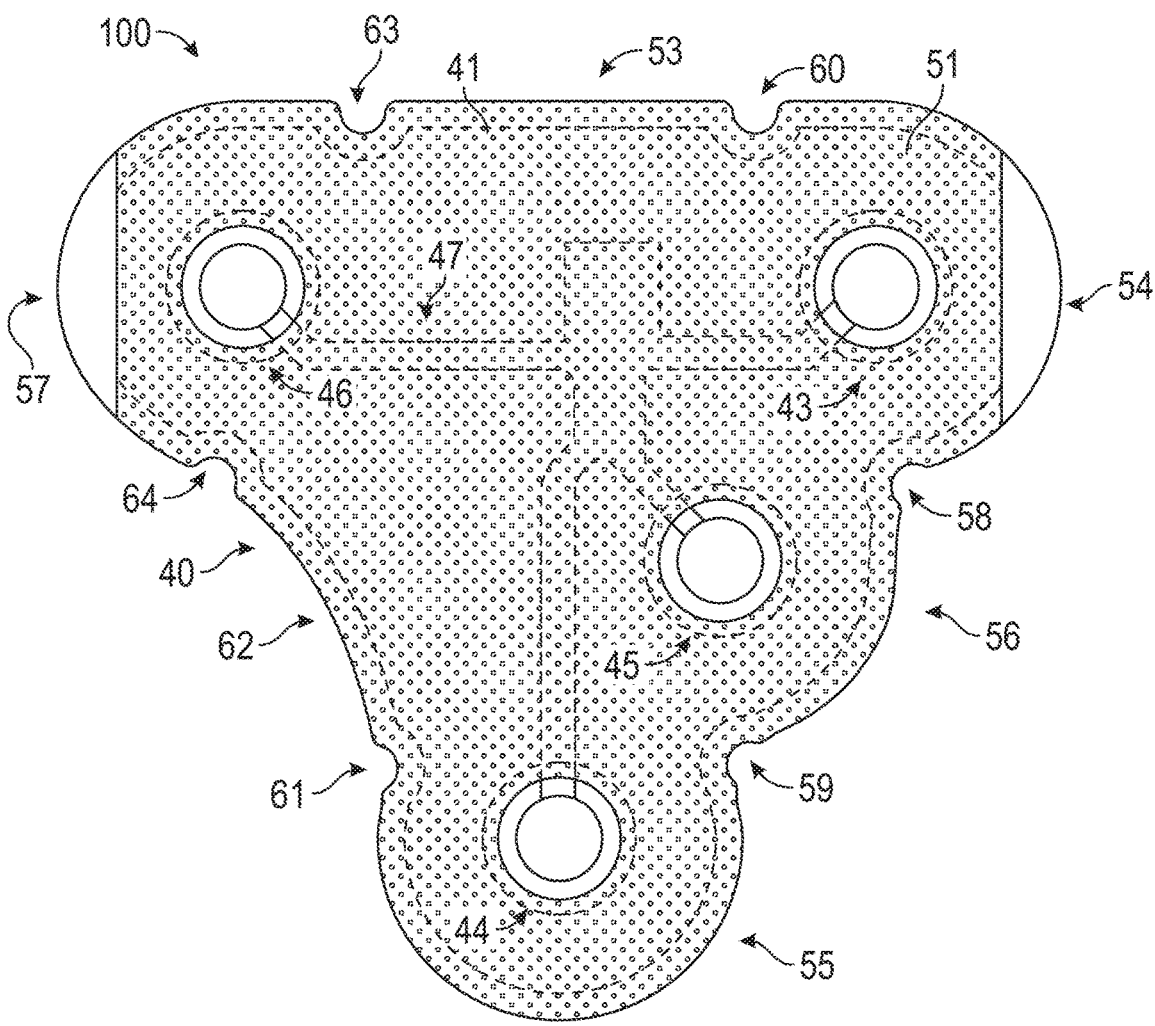
FIG. 4 is a bottom plan view of the system for biometric monitoring as depicted in FIG. 2.
Figure 5:
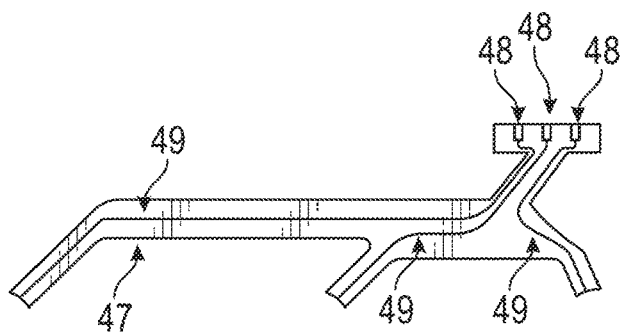
FIG. 5 is a top plan view of the flexible printed circuit of the system for biometric monitoring as depicted in FIG. 1.
Figure 6:
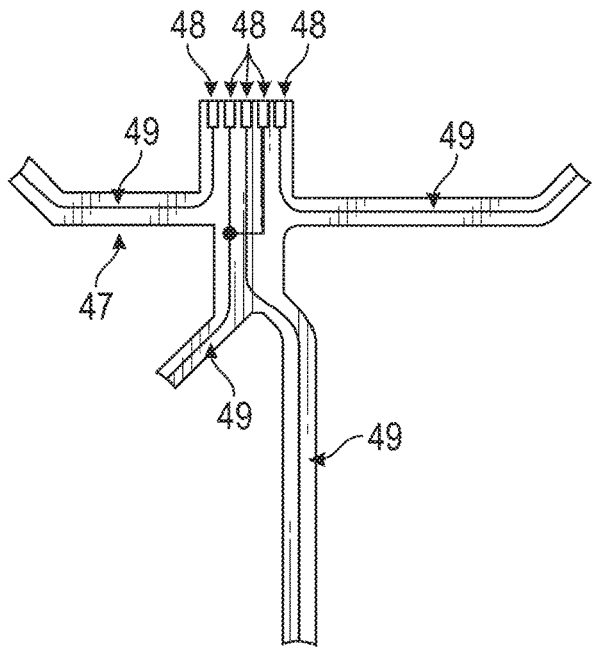
FIG. 6 is a top plan view of the flexible printed circuit of the system for biometric monitoring as depicted in FIG. 2.
Figure 7:
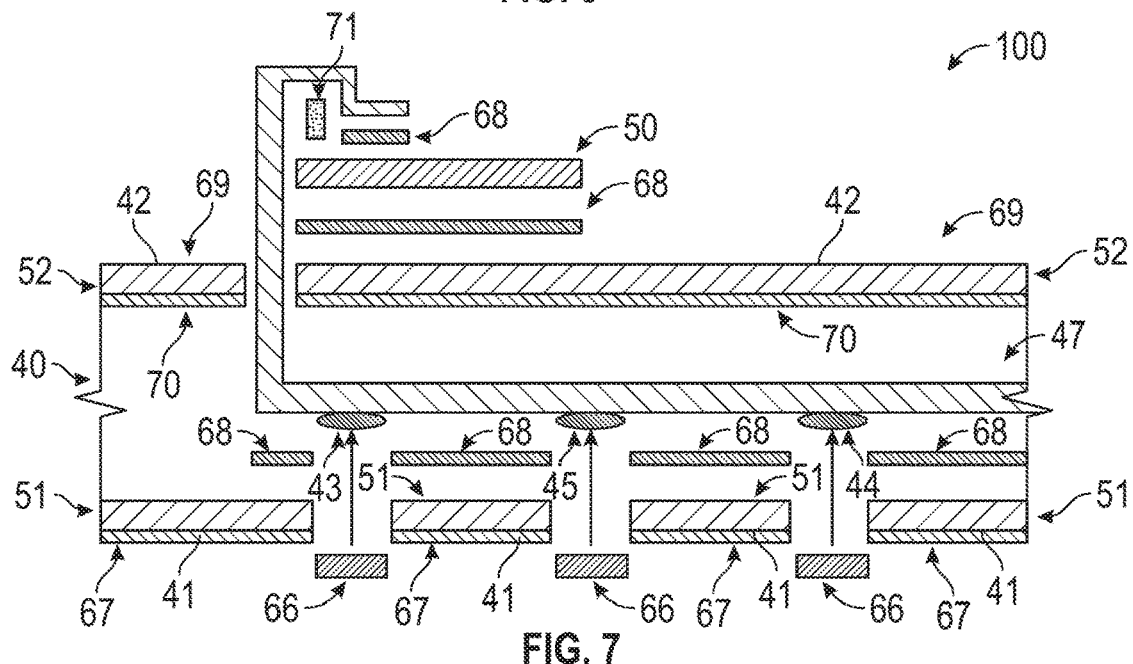
FIG. 7 is a cross-sectional view taken through line 7-7 in FIG. 1.
Figure 8:
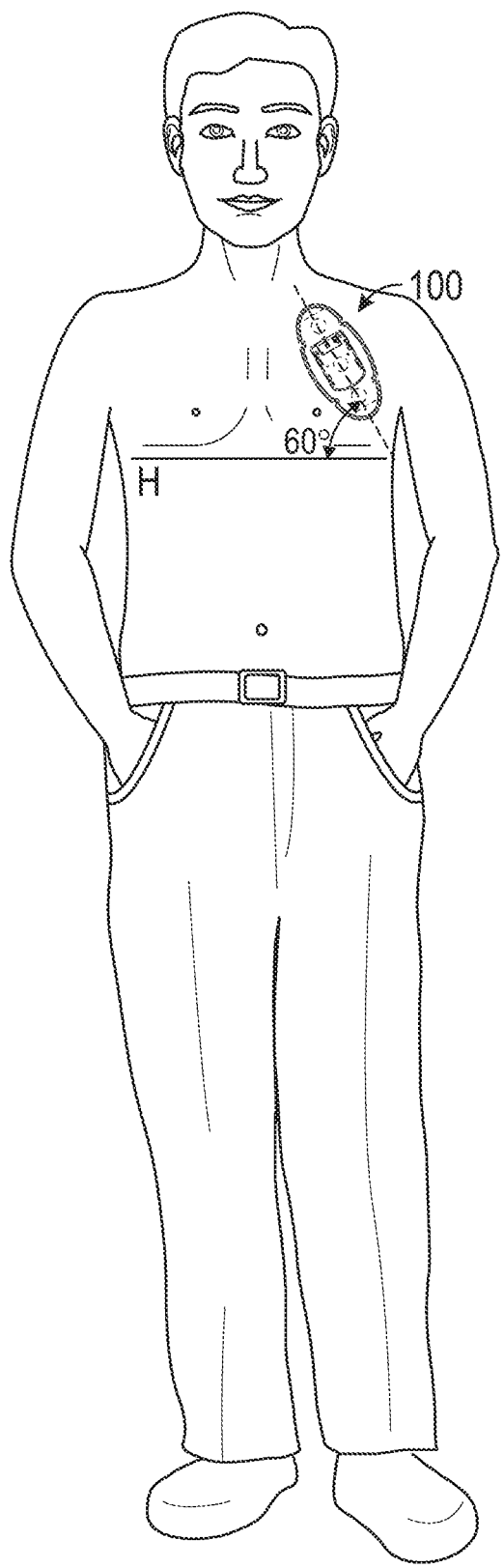
FIG. 8 is an environmental view of the system for biometric monitoring worn by a patient.
Figure 9:
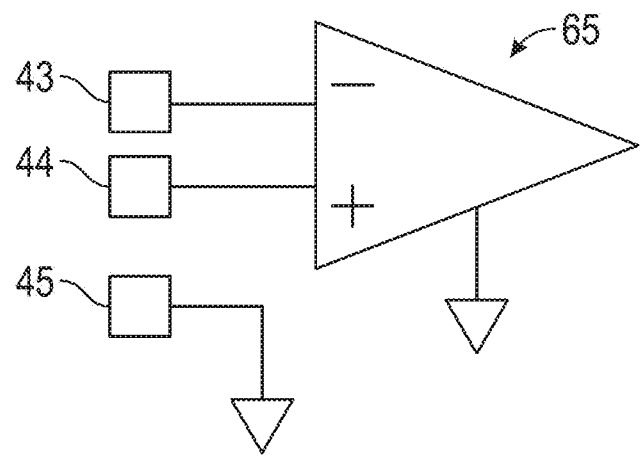
FIG. 9 is a circuit diagram of one embodiment of the invention.
Figure 10:
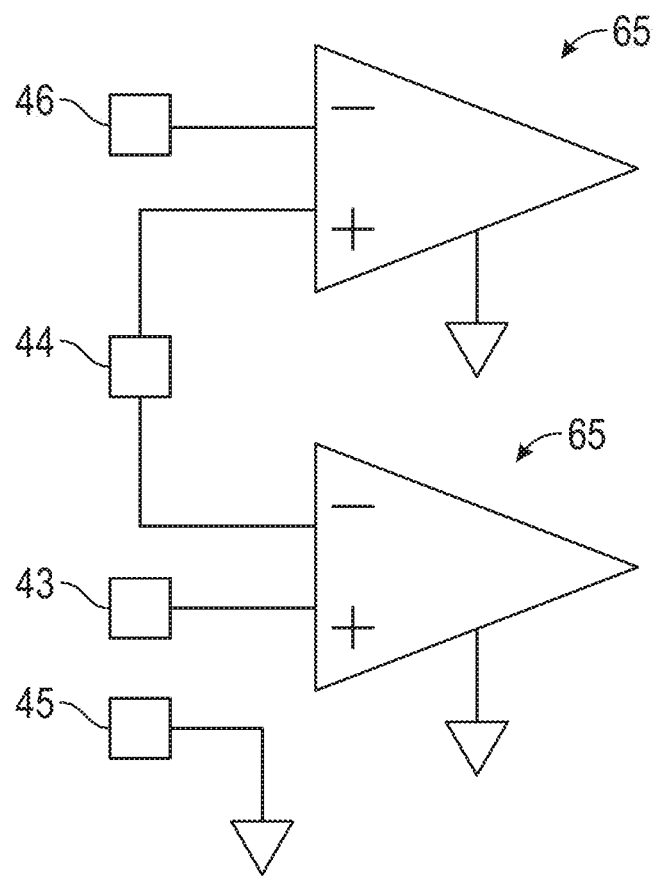
FIG. 10 is a circuit diagram of another embodiment of the invention.

The present invention will now be described more fully hereinafter with reference to the accompanying drawings, in which preferred embodiments of the invention are shown. This invention may, however, be embodied in many different forms and should not be construed as limited to the embodiments set forth herein. Rather, these embodiments are provided so that this disclosure will be thorough and complete, and will fully convey the scope of the invention to those skilled in the art. Those of ordinary skill in the art realize that the following descriptions of the embodiments of the present invention are illustrative and are not intended to be limiting in any way. Other embodiments of the present invention will readily suggest themselves to such skilled persons having the benefit of this disclosure. Like numbers refer to like elements throughout.

Although the following detailed description contains many specifics for the purposes of illustration, anyone of ordinary skill in the art will appreciate that many variations and alterations to the following details are within the scope of the invention. Accordingly, the following embodiments of the invention are set forth without any loss of generality to, and without imposing limitations upon, the claimed invention.

In this detailed description of the present invention, a person skilled in the art should note that directional terms, such as "above," "below," "upper," "lower," and other like terms are used for the convenience of the reader in reference to the drawings. Also, a person skilled in the art should notice this description may contain other terminology to convey position, orientation, and direction without departing from the principles of the present invention.

Furthermore, in this detailed description, a person skilled in the art should note that quantitative qualifying terms such as "generally," "substantially," "mostly," and other terms are used, in general, to mean that the referred to object, characteristic, or quality constitutes a majority of the subject of the reference. The meaning of any of these terms is dependent upon the context within which it is used, and the meaning may be expressly modified.

An embodiment of the invention, as shown and described by the various figures and accompanying text, provides a system for biometric monitoring 100, which may include a patch 40 and electrodes 43, 44, 45, 46. The patch 40 may be adapted to be worn by a patient for an extended period of time without causing irritation to the patient's skin or separating from the patient's skin. The system 100 may include a cradle 50 secured to the patch 40 and adapted to carry a monitoring device and electrically communicate with the electrodes 43, 44, 45, 46 without external wires while biometric information is collected from the patient.

The system 100 may be operated as a single-channel patch or a double-channel patch. In single-channel embodiments, the system 100 may include three electrodes 43, 44, 45. The first electrode 43 may be a right arm electrode. The second electrode 44 may be a left leg electrode. The third electrode 45 may be a reference electrode or right leg electrode. The electrical output of the third electrode 45 may be adapted to be in electronic communication with a reference lead. The electrical output of the third electrode 45 may be in electronic communication with an electrical pad 48. The first electrode 43 and the second electrode 44 may be adapted to be in electronic communication with different inputs to a single operational amplifier 65. Each of the first electrode 43 and the second electrode 44 may have electrical outputs in electronic communication with different electrical pads 48. The electrical pads 48 may be located on the second side 42 of the patch 40. In one embodiment, the electrical pads 48 may be adapted to be in electronic communication with a biometric monitoring device when the device is carried by the cradle 50.

Double-channel embodiments may have four electrodes 43, 44, 45, 46. The first electrode 43 may be a right arm electrode. The second electrode 44 may be a left leg electrode. The third electrode 45 may be a reference electrode or right leg electrode. The fourth electrode 46 may be a left arm electrode. The electrical output of the third electrode 45 may be adapted to be in electronic communication with a reference lead. The electrical output of the third electrode 45 may be in electronic communication with an electrical pad 48. The first electrode 43 and the second electrode 44 may be adapted to be in electronic communication with different inputs to a single operational amplifier 65, The fourth electrode 46 and the second electrode 44 may be adapted to be in electronic communication with different inputs to a different operational amplifier 65. Each of the first electrode 43, second electrode 44, and fourth electrode 46 may have electrical outputs in electronic communication with different electrical pads 48. The second electrode 44 may be in electronic communication with two different electrical pads 48. The electrical pads 48 may be located on the second side 42 of the patch 40, In one embodiment, the electrical pads 48 may be adapted to be in electronic communication with a biometric monitoring device when the device is carried by the cradle 50.

In a system 100 with a single-channel embodiment, the patch 40 may be adhered to a patient at a 60-degree angle with respect to a horizontal line H across the patient's chest.

For optimal performance of the electrodes 43, 44, 46, the electrodes may be positioned no less than a minimum distance from one another. Each electrode 43, 44, 46 providing an electrical input to an operational amplifier 65 may be located a minimum of 8 cm from any other electrode 43, 44, 46 providing an electrical input to an operational amplifier 65. Each electrode 43, 44, 45, 46 may have a diameter of 1.5 cm. Each electrode 43, 44, 45, 46 may be located no less than 1 cm away from an edge of the second layer 52 of the patch 40.

The first electrode 43, second electrode 44, and third electrode 45 may be oriented in a linear configuration along a line extending through their respective center points. The center point of the first electrode 43 may be no less than 8 cm away from the center point of the second electrode 44. In double channel embodiments, the center point of the fourth electrode 46 may be located along a line projected through the center point of the third electrode 45 and at a 90-degree angle to a line projected through the center points of the first electrode 43, second electrode 44, and third electrode 45. In embodiments having a fourth electrode 46, the center point of the fourth electrode 46 is located along a line intersection the center point of the third electrode 45 and forming a 90-degree angle with a line extending through the center points of the first electrode 43, second electrode 44, and third electrode 45. In such a configuration, the fourth electrode 46 may be described as positioned on a line intersecting the center point of the third electrode 45 and substantially normal to the line projected through the center points of first electrode 43 and the second electrode 44.

The patch 40 may be shaped to reduce the area making adhesive contact with a patient's skin. The patch 40 may have a first arcuate edge portion 54 extending around the first electrode 43 and a second arcuate edge portion 55 extending around the second electrode 4. A third arcuate edge portion 56 may extend between a first side of the first electrode 43 and a first side of the second electrode 44. A fourth arcuate edge portion 57 may extend between a second side of the first electrode 43 and a second side of the second electrode 44.

In embodiments having four electrodes 34, 44, 35, 46, a linear top edge 53 may form a top portion of the patch 40 perimeter and may extend parallel to a line segment extending between the first arcuate edge portion 54 and the fourth arcuate edge portion 57. The patch 40 perimeter may have a fifth arcuate edge portion 62 extending between the fourth arcuate edge portion 57 and the second arcuate edge portion 55.

Notches may be incorporated into the perimeter of the patch 40. A notch may be a cut-out, semi-circle, or void located in the perimeter of the patch 40. The notch or combination of notches may assist in removal of the system 100 from the patient's body or aid in extending the wear time. A first notch 58 may be located in the patch perimeter between the first arcuate edge portion 54 and the third arcuate edge portion 56. The first notch 58 may be adjacent both the first arcuate edge portion 54 and the third arcuate edge portion 56, A second notch 59 may be located in the patch perimeter between the second arcuate edge portion 55 and the third arcuate edge portion 56. The second notch 59 may be adjacent both the second arcuate edge portion 55 and the third arcuate edge portion 56. A third notch 60 may be located in the patch perimeter between the first arcuate edge portion 54 and the fourth arcuate edge portion 57. The third notch 60 may be adjacent both the first arcuate edge portion 54 and the fourth arcuate edge portion 57. A fourth notch 61 may be located in the patch perimeter between the second arcuate edge portion 55 and the fourth arcuate edge portion 57, The fourth notch 61 may be adjacent both the second arcuate edge portion 55 and the fourth arcuate edge portion 57.

In embodiments with more than three electrodes 43, 44, 45, 46, the notch configuration may differ from the configuration in embodiments with three or fewer electrodes 43, 44, 45, 46. A first notch 58 may be located in the patch perimeter between the first arcuate edge portion 54 and the third arcuate edge portion 56. The first notch 58 may be adjacent both the first arcuate edge portion 54 and the third arcuate edge portion 56. A second notch 59 may be located in the patch perimeter between the second arcuate edge portion 55 and the third arcuate edge portion 56. The second notch 59 may be adjacent both the second arcuate edge portion 55 and the third arcuate edge portion 56. A third notch 60 may be located in the patch perimeter between the first arcuate edge portion 54 and the linear top edge 53. The third notch 60 may be adjacent both the first arcuate edge portion 54 and the linear top edge 53. A fourth notch 61 may be located in the patch perimeter between the second arcuate edge portion 55 and the fifth arcuate edge portion 62. The fourth notch 61 may be adjacent both the second arcuate edge portion 55 and the fifth arcuate edge portion 62. A fifth notch 63 may be located in the patch perimeter between the fourth arcuate edge portion 57 and the linear top edge 53, The fifth notch 63 may be adjacent both the fourth arcuate edge portion 57 and the linear top edge 53. A sixth notch 64 may be located in the patch perimeter between the fourth arcuate edge portion 57 and the fifth arcuate edge portion 62. The sixth notch 64 may be adjacent both the fourth arcuate edge portion 57 and the fifth arcuate edge portion 62.

The patch 40 may include a first layer 51 with a first side 41 adapted to be adjacent the patient's skin when worn. The patch 40 may also include a second layer 52 adhered to the first layer 51 and having a second side 42 opposing the first side 41. The first layer 51 may have a first perimeter defining a first area. The second layer 52 may have a second perimeter, which defines a second area smaller than the first area. The entire second area may be contained entirely within the first area. The second perimeter may be a located a distance from the first perimeter along an entirety of both perimeters. In one embodiment, the distance between the first and second perimeters may be 6 mm. In another embodiment, the distance between the first and second perimeters may be less than 6.6 mm and greater than 5.4 millimeters. The distance between the first and second perimeters may be constant along the entirety of the perimeters or may vary within a range. This difference in size between the first layer 51 and second layer 52 may extend the wear time of the system 100.

The first layer 51 may be constructed from a non-woven material. The first side 41 of the first layer 51 may have a skin side adhesive 67 located thereon. The skin side adhesive 67 may be adapted to adhere the system 100, weighing up to 50 grams, to the patient's skin for seven days. The first layer 51 may be a single-coated, white polyethylene non-woven material. The skin side adhesive 67 may be a medical grade acrylic adhesive. The skin side adhesive 67 thickness may be 2.4 mil. A white super-calendared glassine paper liner may be adhered to the skin side adhesive 67 prior to the system 100 being adhered to a patient's skin. The glassine paper may be 2.6 mil thick. The first layer 51 may be breathable, moisture resistant, die-cuttable, gamma and Et© sterilizable, and support sustained wear by the patient. The non-woven polyethylene fabric may have a thickness of 20.0 mil.

The second layer 52 may be constructed from a foam material 69 with an adhesive backing 70. The second layer 52 may be a polyolefin foam tape. The second layer 52 may be 22 mils thick and the foam material may be a white closed-cell polyolefin foam with a 20 mil thickness. The adhesive backing 70 may be acrylate and designed for medical or surgical applications. The adhesion to steel with a 180-degree peel may be 24 ounces per inch of width for the second layer 52.

A flexible printed circuit 47 may be carried between the first layer 51 and the second layer 52. The flexible printed circuit may have a plurality of traces 49 providing electrical communication between each of the electrodes 43, 44, 45, 46 and a respective electrical pad 48. One or more resistors may be incorporated into the flexible printed circuit 47. The one or more resistors may be adapted to provide a measurable resistance value to a biometric monitoring device carried by the cradle 50 and allow the biometric monitoring device to identify the type of patch 40 used by the system 100. Each of the electrical pads 48 may be in electrical communication with one of the electrodes 43, 44, 45, 46. Each of the electrodes 43, 44.45, 46 may be in electrical communication with one or more electrical pads 48. The flexible printed circuit 47 may have a front side and an opposing back side. The majority of the front side may be positioned adjacent the first layer 51 and proximate the patient's body when the patch 40 is worn by a patient. Each electrode 43, 44, 45, 46 may be in electrical communication with a respective trace 49.

The electrodes 43, 44, 45, 46 may be positioned to align with apertures located in the first layer 51. Such a configuration may avow each electrode 43, 44, 45.46 to receive an electronic signal from the patient when the patch is worn. Each aperture may be adapted to carry hydrogel 66, which may enhance the quality of electrical communication between the electrodes 43, 44, 45, 46 and the patient. They hydrogel 66 may have a volume resistivity of 1000 ohm-cm maximum. The stainless-steel adhesion of the hydrogel 66 for a 180-degree peel may be a minimum of 240 grams per inch of width on the skin side. The hydrogel 66 may have a nominal thickness of 35 mil and range between 40 and 30 mils. The hydrogel pH may be nominally 3.5 and range between 4.0 and 3.0.

The flexible printed circuit 47 may be adhered to the first layer 51 with double coated tape 68. The double coated tape 68 may be 5 mils thick and located between the flexible printed circuit 47 and the first layer 51. The double coated tape 68 may be medical grade and high adhesion. The adhesive portion of the double coated tape 68 may be synthetic rubber. The 180-degree peel adhesion to stainless-steel may be 175 oz/inch width.

A portion of the flexible printed circuit 47 may extend through an aperture in the second layer 52, which is adapted to receive this portion of the flexible printed circuit 47. This portion of the flexible printed circuit 47 may have the electrical pads 48 located thereon. The flexible printed circuit 47 may bend 360 degrees. The bend in the flexible printed circuit 47 may allow the electrical pads 48 to face upward, opposing the patient's body. The electrical pads 48 may be positioned within the perimeter of the cradle 50. The biometric monitoring device may have external electrical contacts adapted to make an electrical connection with the electrical pads 48 when the biometric monitoring device is carried by the cradle 50. A back side of the flexible printed circuit 47 opposing the electrical pads 48 may be secured to a portion of the cradle 50 using double coated tape 68. A piece of foam 71 may be located between the top side of the cradle 50 and the flexible printed circuit 47. The foam 71 may be a microcellular urethane adhered to the cradle 50.

A cradle 50 may be secured to the second side 42 and adapted to carry a biometric monitoring device. The cradle 50 may adhere to the second layer 52 using double coated tape 68 placed between the cradle 50 and the second side 42 of the second layer 52. The cradle 50 may be carried entirely within a perimeter defined by the second layer 52.

Some of the illustrative aspects of the present invention may be advantageous in solving the problems herein described and other problems not discussed which are discoverable by a skilled artisan.

While the above description contains much specificity, these should not be construed as limitations on the scope of any embodiment, but as exemplifications of the presented embodiments thereof. Many other ramifications and variations are possible within the teachings of the various embodiments. While the invention has been described with reference to exemplary embodiments, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment disclosed as the best or only mode contemplated for carrying out this invention, but that the invention will include all embodiments falling within the scope of the appended claims. Also, in the drawings and the description, there have been disclosed exemplary embodiments of the invention and, although specific terms may have been employed, they are unless otherwise stated used in a generic and descriptive sense only and not for purposes of limitation, the scope of the invention therefore not being so limited. Moreover, the use of the terms first, second, etc. do not denote any order or importance, but rather the terms first, second, etc. are used to distinguish one element from another. Furthermore, the use of the terms a, an, etc. do not denote a limitation of quantity, but rather denote the presence of at least one of the referenced item.

Thus the scope of the invention should be determined by the appended claims and their legal equivalents, and not by the examples given.

That which is claimed is:

1. A system for biometric monitoring comprising:
   a patch having a first side adapted to adhere to a patient's skin and an opposing second side;
   a plurality of electrodes carried by the patch and adapted to be in electrical communication with the patient's skin, further comprising:
   a first electrode, and
   a second electrode;
   a flexible printed circuit carried by the patch and comprising:
   an electrical pad located on a front side,
   a trace located on the front side and adapted to provide electrical communication between one of the plurality of electrodes and the electrical pad;
   a cradle having a back side proximate to and affixed to the second side of the patch and an opposing front side distal the patch;
   wherein the patch comprises:
   a first arcuate edge portion having a first endpoint and a second endpoint, wherein the first arcuate edge portion extends around the first electrode along an outer periphery of the patch,
   a second arcuate edge portion having a first endpoint and a second endpoint, wherein the second arcuate edge portion extends around the second electrode along an outer periphery of the patch,
   a third arcuate edge portion extending from the first endpoint of the first arcuate edge portion to the first endpoint of the second arcuate edge portion along an outer periphery of the patch, and
   a fourth arcuate edge portion extending from the second endpoint of the first arcuate edge portion to the second endpoint of the second arcuate edge portion along an outer periphery of the patch;
   wherein a first portion of a back side of the flexible printed circuit, which directly opposes the electrical pad is affixed to the front side of the cradle;
   wherein a second portion of the flexible printed circuit is positioned between the first side and the second side of the patch with the back side of the flexible printed circuit proximate the cradle and the front side of the flexible printed circuit proximate the plurality of electrodes; and
   wherein the electrical pad is adapted to physically contact and electrically engage an electrical contact located on a biometric monitoring device carried by the cradle.

2. The system according to claim 1 wherein the second electrode has a center positioned at least 8 centimeters away from a center of the first electrode.

3. The system according to claim 1 wherein the patch further comprises:
   a first notch in the patch perimeter adjacent the first arcuate edge portion and the third arcuate edge portion; and
   a second notch in the patch perimeter adjacent the second arcuate edge portion and the third arcuate edge portion.

4. The system according to claim 1 wherein the plurality of electrodes further comprises:
   a third electrode located in a linear configuration between the first electrode and the second electrode, and
   a fourth electrode having a center aligned with a center of the third electrode and positioned substantially normal to a line projected through a center of the first electrode and a center of the second electrode; and
   wherein the fourth arcuate edge portion further comprises:
   a linear top edge extending parallel to a line projected through the center of the first electrode and a center of the fourth electrode,
   a concave edge portion adjoining the second arcuate edge portion.

5. The system according to claim 4 wherein the patch further comprises:
   a first notch in the patch perimeter adjacent the first arcuate edge portion and the third arcuate edge portion;
   a second notch in the patch perimeter adjacent the second arcuate edge portion and the third arcuate edge portion;
   a third notch in the patch perimeter adjacent the first arcuate edge portion and the linear top edge; and
   a fourth notch in the patch perimeter adjacent the second arcuate edge portion and the concave edge portion.

6. The system according to claim 1 wherein the patch further comprises:
   a first layer having a first perimeter and located adjacent the patient's skin; and
   a second layer adhered to the first layer and contained entirely within an area defined by the first perimeter.

7. The system according to claim 6 wherein the cradle is adhered to the second layer and contained entirely within an area defined by a perimeter of the second layer.

8. The system according to claim 6 wherein the first layer comprises a non-woven material.

9. The system according to claim 8 wherein the second layer has a second perimeter between 5.4 millimeters and 6.6 millimeters from the first perimeter along an entirety of the second perimeter.

10. The system according to claim 6 wherein a portion of the flexible printed circuit is carried between the first layer and the second layer, and
    wherein the second layer has an aperture adapted to receive a portion of the flexible printed circuit.

11. The system according to claim 6 wherein the second layer comprises a foam material.

12. The system according to claim 6 wherein each point of a perimeter of each of the plurality of electrodes is at least 1 centimeter away from a perimeter of the second layer.

13. A system for biometric monitoring comprising:
    a first electrode;
    a second electrode with a center positioned at least 8 centimeters away from a center of the first electrode;
    a patch having a first side adapted to adhere to a patient's skin and an opposing second side, further comprising:
    a first layer comprising a non-woven material, having a first perimeter and located adjacent the patient's skin,
    a second layer comprising a foam material, adhered to the first layer, contained entirely within an area defined by the first perimeter, and having an aperture, a first arcuate edge portion having a first endpoint and a second endpoint, wherein the first arcuate edge portion extends around the first electrode along an outer periphery of the patch,
a second arcuate edge portion having a first endpoint and a second endpoint, wherein the second arcuate edge portion extends around the second electrode along an outer periphery of the patch,
a third arcuate edge portion extending from the first endpoint of the first arcuate edge portion to the first endpoint of the second arcuate edge portion along an outer periphery of the patch,
a fourth arcuate edge portion extending from the second endpoint of the first arcuate edge portion to the second endpoint of the second arcuate edge portion along an outer periphery of the patch,
a first notch in the patch perimeter adjacent the first arcuate edge portion and the third arcuate edge portion, and
a second notch in the patch perimeter adjacent the second arcuate edge portion and the third arcuate edge portion;
a flexible printed circuit extending through the aperture, wherein at least a portion is carried between the first layer and the second layer, comprising:
an electrical pad located on a front side;
a trace located on the front side and adapted to provide electrical communication between the first electrode and the electrical pad; and
a cradle having a back side proximate to and affixed to the second side of the patch and an opposing front side distal the patch;
wherein the patch is adapted to carry the first electrode and the second electrode in electrical communication with the patient's skin;
wherein a first portion of a back side of the flexible printed circuit, which directly opposes the electrical pad is affixed to the front side of the cradle;
wherein a second portion of the flexible printed circuit is positioned between the first side and the second side of the patch with the back side of the flexible printed circuit proximate the cradle and the front side of the flexible printed circuit proximate the plurality of electrodes; and
wherein the electrical pad is adapted to physically contact and electrically engage an electrical contact located on a biometric monitoring device carried by the cradle.

14. The system according to claim 13 wherein the cradle is adhered to the second layer and contained entirely within an area defined by a perimeter of the second layer.

15. The system according to claim 13 wherein the second layer has a second perimeter a minimum distance between 5.4 millimeters and 6.6 millimeters from the first perimeter along an entirety of the second perimeter.

16. The system according to claim 15 wherein each point of a perimeter of both the first electrodes and the second electrode is at least 1 centimeter away from the perimeter of the second layer.

17. A system for biometric monitoring comprising:
a first electrode;
a second electrode with a center positioned at least 8 centimeters away from a center of the first electrode;
a third electrode located in a linear configuration between the first electrode and the second electrode;
a fourth electrode having a center aligned with a center of the third electrode and positioned to form a ninety-degree angle between a line-projected through a center of the first electrode and a center of the second electrode;
a patch having a first side adapted to adhere to a patient's skin and an opposing second side, further comprising:
a first layer comprising a non-woven material, having a first perimeter and located adjacent the patient's skin,
a second layer comprising a foam material, adhered to the first layer, contained entirely within an area defined by the first perimeter, having a second perimeter a minimum distance between 5.4 millimeters and 6.6 millimeters from the first perimeter along an entirety of the second perimeter, and having an aperture,
a first arcuate edge portion having a first endpoint and a second endpoint, wherein the first arcuate edge portion extends around the first electrode along an outer periphery of the patch,
a second arcuate edge portion having a first endpoint and a second endpoint, wherein the second arcuate edge portion extends around the second electrode along an outer periphery of the patch,
a third arcuate edge portion extending from the first endpoint of the first arcuate edge portion to the first endpoint of the second arcuate edge portion along an outer periphery of the patch,
a fourth arcuate edge portion extending from the second endpoint of the first arcuate edge portion to the second endpoint of the second arcuate edge portion along an outer periphery of the patch, wherein the fourth arcuate edge portion further comprises:
a concave edge portion adjoining the second arcuate edge portion, and
a linear top edge extending parallel to a line projected through the center of the first electrode and a center of the fourth electrode;
a first notch in the patch perimeter adjacent the first arcuate edge portion and the third arcuate edge portion,
a second notch in the patch perimeter adjacent the second arcuate edge portion and the third arcuate edge portion,
a third notch in the patch perimeter adjacent the first arcuate edge portion and the linear top edge,
a fourth notch in the patch perimeter adjacent the second arcuate edge portion and the concave edge portion,
a flexible printed circuit extending through the aperture, wherein at least a portion is carried between the first layer and the second layer, comprising:
an electrical pad located on a front side, and
a trace located on the front side and adapted to provide electrical communication between the first electrode and the electrical pad; and
a cradle having a back side proximate to and adhered to the second layer and an opposing front side distal the second layer, wherein a perimeter of the cradle is contained entirely within an area defined by a perimeter of the second layer;
wherein the patch is adapted to carry the first electrode, second electrode, third electrode, and fourth electrode in electrical communication with the patient's skin;
wherein a first portion of a back side of the flexible printed circuit, which directly opposed the electrical pad is affixed to the front side of the cradle;

wherein a second portion of the flexible printed circuit is positioned between the first layer and the second layer of the patch with the back side of the flexible printed circuit proximate the second layer and the and the front side of the flexible printed circuit proximate the first layer; and wherein the electrical pad is adapted to physically contact and electrically engage an electrical contact located on a biometric monitoring device carried by the cradle; and wherein each point of a perimeter of each of the first electrode, the second electrode, the third electrode, and the fourth electrode is at least 1 centimeter away from the second perimeter.

* * * * *